(12) United States Patent
Small et al.

(10) Patent No.: US 6,911,506 B2
(45) Date of Patent: Jun. 28, 2005

(54) CATALYST COMPOSITION AND OLEFIN POLYMERIZATION USING SAME

(75) Inventors: Brooke L. Small, Kingwood, TX (US); Angel Jose Marcucci, Sugar Land, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 230 days.

(21) Appl. No.: 10/013,144

(22) Filed: Dec. 10, 2001

(65) Prior Publication Data

US 2003/0149198 A1 Aug. 7, 2003

(51) Int. Cl.[7] .............................. C08F 4/44; B01J 31/23
(52) U.S. Cl. ........................ 526/161; 526/171; 526/172; 502/155; 502/167
(58) Field of Search ................................ 526/161, 171, 526/172; 502/155, 167

(56) References Cited

U.S. PATENT DOCUMENTS

| | | | |
|---|---|---|---|
| 4,096,093 A | 6/1978 | Hwang ........................ 252/430 |
| 5,955,555 A | * 9/1999 | Bennett ....................... 526/133 |
| 6,103,657 A | 8/2000 | Murray ........................ 502/155 |
| 6,103,946 A | 8/2000 | Brookhart, III et al. .... 585/523 |
| 6,184,171 B1 | 2/2001 | Shih ........................... 502/158 |
| 6,211,370 B1 | 4/2001 | Jacobsen et al. .............. 546/25 |
| 6,458,905 B1 | 10/2002 | Schmidt et al. ............. 526/172 |
| 2002/0028941 A1 | 3/2002 | De Boer et al. ............. 546/167 |

FOREIGN PATENT DOCUMENTS

| | | | | |
|---|---|---|---|---|
| EP | 1188762 | 9/2000 | | |
| WO | WO00/20427 | 4/2000 | | |
| WO | WO00/20427 A1 | 4/2000 | ........... | C07F/19/00 |
| WO | WO00/20467 | 4/2000 | | |
| WO | WO00/69923 A1 | 11/2000 | ........... | C08F/10/00 |
| WO | WO00/69923 | 11/2000 | | |
| WO | WO00/78826 A1 | 12/2000 | ........... | C08F/10/00 |
| WO | WO01/10875 | 2/2001 | | |
| WO | WO01/10875 A1 | 2/2001 | ........... | C07F/15/02 |
| WO | WO01/58874 | 8/2001 | | |
| WO | WO 01/74830 | * 10/2001 | | |
| WO | WO02/00339 | 2/2002 | | |
| WO | WO02/28805 | 4/2002 | | |
| WO | WO02/34746 | 5/2002 | | |
| WO | WO03/011876 | 2/2003 | | |

OTHER PUBLICATIONS

*Highly Active Iron and Cobalt Catalysts for the Polymerization of Ethylene*, Brooke L. Small, Maurice Brookhart, and Alison M.A. Bennett, *Journal of the American Chemical Society*, vol., 120, No. 16, Pp. 4049–4050, 1998.

*Polymerization of Propylene by a New Generation of Iron Catalysts: Mechanisms of Chain Initiation, Propagation, and Termination*, Brooke L. Small and Maurice Brookhart, *Macromolecules*, vol. 32, No. 7, Pp. 2120–2130, 1999.

*Preparation, Structure, and Ethylene Polymerixation Behavior of Bis(imino)pyridyl Chromium (III) Complexes*, Miguel A. Esteruelas, et al., *Organometallics*, vol. 22, No. 3, pp. 395–406, 2003.

*Iron–Based Catalysts with Exceptionally High Activities and Selectivities for Oligomerization of Ethylene to Linear α–Olefins*, Brooke L. Small and Maurice Brookhart, *Journal of the American Chemical Society*, vol. 120, No. 28, Pp. 7143–7144, 1998.

Small. et al, "Polymerization of Propylene by a New Generation of Iron Catalysts: Mechanisms of Chain Initiation, Propagation, and Termination," *Macromolecules* 1999, 32:7:2120–2130.

* cited by examiner

*Primary Examiner*—Robert D. Harlan
(74) *Attorney, Agent, or Firm*—Conley, Rose, P.C.; Rodney B. Carroll; Joe D. Hulett

(57) ABSTRACT

Novel metal complexes, particularly chromium complexes, which contain at least one tridentate ligand are disclosed and prepared. Olefins, particularly ethylene, can be reacted to form butene and/or other homo- or co-oligomers and/or polymers with high α-olefin concentrations by contacting a metal catalyst which contains a transition metal, particularly chromium, complexes having per metal atom at least one tridentate ligand with N, O, or N and O coordinating sites.

15 Claims, No Drawings

CATALYST COMPOSITION AND OLEFIN POLYMERIZATION USING SAME

FIELD OF THE INVENTION

This invention relates to novel metal complexes, particularly chromium complexes, which contain at least one tridentate ligand for each metal. This invention also relates to an improved olefin polymerization process catalyzed by a catalyst composition, which comprises such novel metal complexes. The polymerization process is particularly useful for making 1-butene and a wide range of oligomeric and polymeric products having high α-olefin concentrations.

BACKGROUND

Many linear olefins, particularly linear α-olefins, typically have a variety of valuable uses. For example, α-olefins, such as 1-hexene, can be used in hydroformylation (so-called "OXO" process) to produce oxygenated products like alcohols and aldehydes. In addition to finding uses in specialty chemicals or as intermediates, α-olefins also can be used in polymerization processes as either a monomer or co-monomer to prepare polyolefins, or other polymers. For example, it has been widely reported that 1-octene can form polymers or co-polymers, which may be used as effective drag reducing agents for transporting hydrocarbons in pipelines, It is therefore desirable to control the linearity of the product, or produce linear olefins, particularly linear α-olefins, in most oligomerization or polymerization processes.

It is well known that mono-olefins, particularly lower α-olefins, particularly ethylene, propylene, and 1-butene can be oligomerized (including dimerized and trimerized) and/or polymerized by using homogeneous or heterogeneous catalyst systems comprising compounds derived from transition metals such as titanium, zirconium, vanadium, chromium, nickel and/or other metals, either unsupported or on a support such as alumina, silica, silica-alumina, titania, other refractory metal oxides, and other similar materials. Even diene monomers such as 1,3-butadiene may be oligomerized or polymerized to give various products such cyclooctadienes. These polymerization catalyst systems frequently are used with an organometallic co-catalyst, such as organoboron, organoaluminum and/or organotin compounds.

Many catalyst systems are usually not very selective in the production of oligomeric or polymeric olefinic products in terms of molecular weight distribution, linearity of the carbon-carbon backbone, branching, location of the double bond(s) in the product, and incorporation of co-monomers, if any, into the product. Some reported homogeneous organometallic catalyst systems tend to have lower activities, higher consumptions of co-catalysts, but they can produce lower molecular weight oligomers or polymers with a narrow molecular weight distribution.

As a result, there is always a need of improving the catalyst systems to have better catalytic properties in terms of controlling specific oligomerization or polymerization of specific olefins or diolefins to produce products with the desired or targeted physical and chemical properties.

SUMMARY OF THE INVENTION

It is one objective of the present invention to provide a polymerization process for making a product, the polymerization process comprises contacting at least one olefin in a feed, with or without a medium, with a catalyst and a co-catalyst, followed by recovering the product, wherein the catalyst comprises a metal-tridentate ligand complex comprising a metal, preferably a transition metal, one or more tridentate ligands (such as FORMULA A) having at least two different elements for the three coordinating sites in each tridentate ligand, the elements are independently selected from the group consisting of nitrogen, phosphorus, oxygen, and sulfur, and wherein the metal-tridentate ligand complex has a formula as FORMULA B.

It is another object that the olefin to be polymerized includes, but is not limited to, mono-olefins (α-olefins and internal olefins; linear and branched olefins) like ethylene, propylene, 1-butene, cis-2-butene, trans-2-butene, 1-pentene, 3-methyl-1-pentene, 4-methyl-4-methyl-1-pentene, 1-hexene, 1-heptene, 1-octene, vinylcyclohexane, cyclopentene, methylcyclopentene (1-, 2-, 3- or mixtures), 1-octadecene, and mixtures of mono-olefins; dienes like 1,3-butadiene, isoprene, 1,4-pentadiene, 1,3-hexadiene, 1,4-hexadiene and 1,5-hexadiene, 4-vinylcyclohexene, vinylnorbornene, norbornadiene, and mixtures of dienes; vinyl-aromatic compounds such as 1- or 2-vinylnaphthalene, 2- or 4-vinylpyridine, styrene and substituted styrenes like o-methylstyrene, m-methylstyrene, p-methylstyrene, p-ethylstyrene, divinylbenzene, and p-t-butylstyrene; and mixtures thereof; and mixtures of mono-olefins, dienes and/or vinyl-aromatic compounds.

It is a further object to provide a catalyst composition which comprises a metal-tridentate ligand complex having a structure of FORMULA B, wherein M consists essentially of an element selected from the group consisting of manganese, chromium, vanadium, nickel, and mixtures thereof; the co-catalyst comprises one or more aluminum alkyl compounds or organoboron compounds, or mixtures thereof; and the product comprises α-olefins, which can be linear, branched, or mixtures thereof. In another embodiment, the product can be characterized by having Schulz-Flory constants (K) in the range of from about 0.4 to about 0.98, preferably from about 0.5 to about 0.9, more preferably from about 0.55 to about 0.8.

It is another object to provide an ethylene dimerization process for making 1-butene, the dimerization process comprises contacting ethylene in a feed, with or without a medium, with a catalyst and a co-catalyst, followed by recovering 1-butene, wherein the catalyst comprises a metal-tridentate ligand complex comprising a transition metal, one or more tridentate ligands (such as FORMULA A) having nitrogen for all three coordinating sites in the tridentate ligand, and wherein the metal-tridentate ligand complex has a formula as FORMULA B. Depending on $R^{11}$ and $R^{15}$, high 1-butene purity (in excess of 98%, preferably in excess of 99% or higher, among the butene isomers) may be obtained.

Another object of the present invention to provide a catalyst composition which comprises a metal-tridentate ligand complex comprising a structure of FORMULA B.

It is a further object to provide a catalyst composition which comprises a metal-tridentate ligand complex comprising a structure of FORMULA B, wherein $Q^1$, and $Q^2$ are nitrogen, $Q^3$ is oxygen, and $R^4$ does not exist; $R^1$ and $R^3$ are independently selected from $C_1$ to $C_5$ alkyl groups; $R^2$ is selected from 1-ring aryl groups; $R^5$ $R^6$, and $R^7$ are independently selected from H and $C_1$ to $C_5$ alkyl groups; L is selected from F, Cl, Br, I and mixtures thereof; and q is 2.

It is another object of the present to provide a chromium chloride complex containing 6-[1-{(2,6-dimethylphenyl)imino}ethyl]-2-acetylpyridine.

It is yet another object of the present to provide a chromium chloride complex containing 6-[1-{(2,6-diisopropylphenyl)imino}ethyl]-2-acetylpyridine.

It is still another object to provide a method for making the metal complexes with suitable transition metal starting materials and suitable ligands under conditions effective to produce such complexes.

It is yet another object to provide a method for making the suitable tridentate ligands, which are useful for making the metal complexes.

Another object is to provide a multi-component catalyst system comprising (a) at least one first component consisting essentially of an ethylene or propylene dimerization or trimerization catalyst comprising a metal-tridentate ligand complex described herein, such as FORMULA B containing a first transition metal, and with nitrogen for all three coordinating sites, and (b) at least one second component consisting essentially of an ethylene or propylene polymerization catalyst such as a Ziegler-Natta catalyst, a precursor of the Ziegler-Natta catalyst, a metallocene, a precursor of the metallocene, and mixtures thereof. The second component contains a second transition metal. It is preferred to use one or more co-catalysts such as organometallic compounds with the multi-component catalyst system to produce ethylene or propylene polymers.

A further object is to provide an olefin polymerization process using a multi-component catalyst system, an organometallic co-catalyst, and the olefin being selected from ethylene, propylene and mixtures thereof in a feed under condition effective to produce polymers, wherein the multi-component catalyst system comprises (a) at least one first component consisting essentially of an ethylene or propylene dimerization or trimerization catalyst, which comprises a metal-tridentate ligand complex described herein, such as FORMULA B and containing a first transition metal, with nitrogen for all three coordinating sites, and (b) at least one second component consisting essentially of an ethylene or propylene polymerization catalyst such as a Ziegler-Natta catalyst, a precursor of the Ziegler-Natta catalyst, a metallocene, a precursor of the metallocene, and mixtures thereof. The second component contains a second transition metal. The polymers are characterized by being a product selected from the group consisting of polyethylene (PE), low density polyethylene (LDPE), linear low density polyethylene (LLDPE), polypropylene (PP), wax, and mixtures thereof.

Other additional objects and advantages will become apparent to and appreciated by those skilled in the art by reading the disclosures herein.

DETAILS OF THE INVENTION

The present invention relates to novel metal-ligand, particularly metal-tridentate ligand complexes, the method for making such complexes, and olefin polymerization processes using catalysts comprising such complexes. The present invention also relates to a novel multi-component catalyst system, which system comprises (a) at least one first component consisting essentially of such a metal-multidentate ligand complex and (b) at least one second component consisting essentially of at least one Ziegler-Natta catalyst or its precursor or a metallocene or a metallocene precursor or mixtures thereof; and a polymerization process using such multi-component catalyst in the presence of an organometallic co-catalyst. For the instant invention and disclosure, the term "polymerization" is used interchangeably, unless otherwise specifically specified or claimed, with the term "oligomerization" to encompass generally (co-)dimerization, (co-)trimerization, homo- or co-oligomerization, and homo- or co-polymerization of one or more olefins (alkenes), vinyl aromatics, and/or diolefins to form (co-)dimers, (co-)trimers, homo- or co-oligomers and/or homo- or co-polymers of the olefin(s) in a feed.

Suitable metal-ligand complexes comprise a metal, a bidentate, tridentate or multidentate ligand, other ligands/moieties/counter-ions to balance the electrical (ionic) charge so that the whole complex is neutral and/or the formal electron count is satisfied, and optionally solvent molecules. Two or more metal atoms, same or different and with or without direct metal-metal bonds may be present in a complex.

Unless a specific ligand is used or referred to, the word "multidentate" is used to denote a ligand having two, three or more coordinating sites. Many ligands having different number and/or type of coordinating sites can be used for the present invention. Tridentate ligands are preferred for the present invention. It is more preferred to have at least two different elements (for instance, N and O) for the three coordinating sites of the three per tridentate ligand. For ethylene dimerization to 1-butene, it is preferred to have nitrogen for all of the three coordinating sites; it is more preferred to have either $R^{11}$ or $R^{15}$ being selected from the group consisting of methyl (Me), ethyl (Et), n-propyl (nPr), iso-propyl (iPr), and n-butyl (nBu). For making wax, it is preferred to have either $R^{11}$ or $R^{15}$ being a t-butyl group.

A more preferred tridentate ligand has the following FORMULA A.

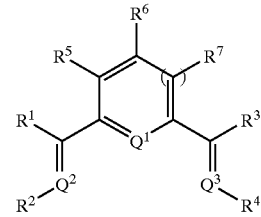

wherein $Q^1$, $Q^2$, and $Q^3$: independently selected from O, S, N, and P;

$R^1$ and $R^3$: independently selected from H, $C_1$ to $C_{20}$ alkyl groups, 1-, 2- or 3- (i.e. 1–3) ring aryl groups and substituted aryl groups;

$R^2$ and $R^4$: if $Q^2$ or $Q^3$ is O or S, none
  if $Q^2$ or $Q^3$ is either N or P, independently selected from H, $C_1$ to $C_{20}$ alkyl groups, 1-, 2- or 3-ring aryl groups and substituted aryl groups;

$R^5$, $R^6$, and $R^7$: independently selected from H, $C_1$ to $C_{20}$ alkyl groups; and $R^7$ does not exist if the carbon to which it is attached is not present.

It is understood that with or without $R^7$ and the associate carbon to which it is attached, the ring containing $Q^1$ is characterized by and should have some aromatic characteristics. For instance, $Q^1$ may be oxygen and the ring is based on a five-membered ring furan structure.

Depending primarily on the starting materials for the metal(s) and the nature of the multidentate ligands, there may be other ligands or moieties or ions present in the complex to balance the electrical (ionic) charges and/or formal electron counts. For instance, if chromium (II) chloride, or $CrCl_2$, is used as the starting material for chromium, chloride will be present in the metal-ligand complex. The number and type of the ligands present may vary, depending on the oxidation state of the metal in the starting material, whether there is any redox reaction taking place, whether the multidentate ligand is used in an ionic form with its own counter-ions, the number of metals in the complex, and other reaction conditions. There may be other reactants, either organic or inorganic, such as acids, salts, bases, and mixtures with different ions present in the reaction, which may end up in the final product.

"L" can be any anions or neutral molecules such as CO. Some non-limiting examples of "L" include CO, H, hydroxide (OH), halides and pseudo-halides, chlorate, chlorite, phosphate, phosphite, sulfate, sulfite, nitrate, amides, alkoxides and their analogues (including those derived from glycols, thiols and phenols), carboxylates (including dicarboxylates and substituted carboxylates such as 2-ethylhexanoate and triflates), hydrocarbyls like alkyls (such as methyl, ethyl, and others), alkenyls, aryls (such as phenyl, methylphenyls, and the like), and mixtures thereof. More examples are further disclosed below in association with FORMULA B.

Because the complex preparation is generally more conveniently carried out in a solution, there may be one or more solvents present during the reaction and/or in the final complex. If one of the reactants is a liquid or the reaction is conducted in a melt-phase, a solvent is not needed for this convenience. As long as a solvent or solvent mixture does not interfere with the metal-multidentate ligand complex formation, it can be used. Depending on the nature of the solvent, the metal complex and the recovery methods/conditions, one may find that there is no solvent in the recovered complex. It is also possible to find by chemical analyses that the number of solvent molecules per metal may be fractional.

Examples of a suitable solvent include both organic and inorganic solvents and their mixtures, such as alcohols (methanol, ethanol, 1- or 2-propanol, sec-butanol, n-butanol, t-butanol, ethylene glycol, propylene glycol, mixtures thereof, or mixtures with water), ethers (dimethyl ether, diethyl ether, methyl ethyl ether, tetrahydrofuran or THF, tetrahydropyran, 1,3-dioxane, 1,4-dioxane and mixtures thereof), glycol ethers, esters (methyl acetate, ethyl acetate, etc), thioethers, halogenated hydrocarbons (such as CFC's [chlorofluoro hydrocarbons], methyl chloride, methyl bromide, methyl iodide, dichloromethane, dibromomethane, chloroform, ethylene dichloride and others), aliphatic and aromatic hydrocarbons, and mixtures thereof. Many of these solvents, such as oxygenated solvents (an ether like THF is an example) can be characterized as Lewis base solvents (i.e. electron pair donating solvents). Additional examples are disclosed below in FORMULA B.

A metal-tridentate ligand complex suitable for the present invention is of the following general FORMULA B:

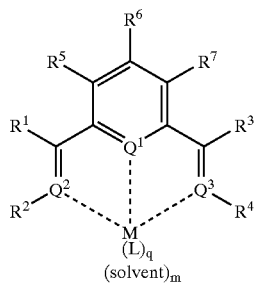

wherein
$Q^1$, $Q^2$, and $Q^3$: independently selected from O, S, N, and P;

$R^1$ and $R^3$: independently selected from H, $C_1$ to $C_{20}$ alkyl groups, 1-, 2- or 3- (i.e. 1–3) ring aryl groups and substituted aryl groups;

$R^2$ and $R^4$: if $Q^2$ or $Q^3$ is O or S, none
    if $Q^2$ or $Q^3$ is either N or P, independently selected from H, $C_1$ to $C_{20}$ alkyl groups, 1-, 2- or 3- (i.e. 1–3) ring aryl groups and substituted aryl groups;

$R^5$, $R^6$, and $R^7$: independently selected from H, $C_1$ to $C_{20}$ alkyl groups;

M: a first transition metal selected from the group consisting of Cr, Mn, V, Ni, Ti, Zr, Hf, Ta, and mixtures thereof;

L: each L independently selected from the group consisting of F, Cl, Br, I, $C_1$ to $C_{20}$ alkyl, $C_5$ to $C_{14}$ aryl, nitrate, $OR^{21}$, $OC(=O)R^{22}$; $R^{23}$; CN; SCN, CO, H, wherein $R^{21}$, $R^{22}$, and $R^{23}$ are independently selected from the group consisting of H, $C_1$ to $C_{20}$ alkyl groups, substituted alkyl groups, 1-, 2- or 3-ring aryl groups, substituted aryl groups, and silyl groups;

solvent selected from the group consisting of ethers, polyethers, esters, alcohols, halogenated hydrocarbons, and mixtures thereof;

q 0–5 (integer) to balance overall electrical charge
m 0–10 (integer or fractional).

As understood from the chemical formula/structure of FORMULA B, the metal complex must comprise at least one metal, preferably a first transition metal and at least one tridentate ligand. As discussed earlier, the number of other ligands (L) would depend on the net electric (used interchangeably with ionic) charge of the M-Ligand so as to make the entire formula neutral. Also as discussed earlier, the number of solvent molecules may vary, depending on the complex, solvent(s), preparation method and many other factors and "m" need not be an integer as determined by chemical analyses. In other words, "m" may be fractional (per metal).

The scope of the present invention encompasses many different metals, M, particularly transition metals, such as titanium, zirconium, hafnium, vanadium. niobium, tantalum. chromium, manganese, iron, nickel, cobalt, and mixtures thereof. It is preferable that M consists essentially of an element selected from the group consisting of chromium, manganese, vanadium, and mixtures thereof. Chromium is a more preferred metal.

Many different sources of these metals may be used to prepare the metal-ligand complexes. These sources include, as discussed earlier, metal halides, pseudo halides, carboxylates, alkoxides, phenoxides, nitrates, sulfates, phosphates, chlorates, organometallic compounds, metal carbonyls, metal clusters and mixtures thereof. Different oxidation states may be used. For instance, many of these materials may be purchased from commercial sources such as Aldrich Chemical Company, Fluka Chemical Company, Alfa AESAR Chemical Company, etc.

More specifically for chromium (oxidation states from 0 to VI), the following materials may be used: chromium(II) chloride, chromium(III) chloride, chromium(II) fluoride, chromium(III) fluoride, chromium (II) bromide, chromium (III) bromide, chromium(II) iodide, chromium(III) iodide, chromium(II) acetate, chromium (III) acetate, chromium (III) acetylacetonate, chromium(II) 2-ethylhexanoate, chromium (II) triflate, chromium(III) nitrate, $Cr(CO)_6$, and mixtures thereof.

As mentioned briefly above, L can be any suitable anion or neutral molecule. If one or more "L's" are needed to balance the charge of FORMULA B to zero, then each "L" is independently selected from the group consisting of CO, H, halides (F, Cl, Br, I,), nitrate, alkoxides or phenoxides ($OR^{21}$), carboxylates [$OC(=O)R^{22}$], $R^{23}$, CN, SCN, and CO. $R^{21}$, $R^{22}$, and $R^{23}$ are independently selected from the group consisting of H, $C_1$ to $C_{20}$ alkyl groups, substituted alkyl groups, 1-, 2- or 3-ring aryl groups, substituted aryl groups and other hydrocarbyl groups such as alkenyl groups. The substituents on the alkyl or aryl groups include, but are not limited to alkyls, aryls, halides, silyl groups, amino groups, alkoxy groups and mixtures thereof. In addition, L can also be selected from hydrocarbyls such as alkyl, alkenyl, or aryl groups. Examples of suitable alkyl groups include, but are not limited to $C_1$ to $C_{20}$ linear or branched alkyls, such as methyl, ethyl, n-propyl, isopropyl, n-butyl, iso-butyl, t-butyl, sec-butyl, 1-octyl groups and others. $C_3$ to about $C_{20}$ linear or branched alkenyl groups also may be used. Examples of suitable aryl groups include, but are not limited to $C_5$ to $C_{14}$ aryls such as 4-pyridyl, 2-pyridyl, phenyl, p-methylphenyl, o-methylphenyl, etc. It is preferred to have halogens as L. It is more preferred the L is or consists of or consists essentially of Cl.

If two or more L's are needed, then they can be independently selected from all of those described and disclosed above, or from moieties containing two or more such groups. For instance, if two L's are needed or preferred, then a glycol type (LL), i.e. —O—$CH_2$—$CH_2$—O— or —O—$CH_2$—$CH(CH_3)$—O— can be used. It is also within the scope of the invention to have mixed (LL') type where the chelating groups are not identical. The above propylene glycol type is one example. Other examples include moieties with mixed alkoxides with phenoxides and/or carboxylates.

It is preferred that $Q^1$ is nitrogen (N). Hydrogen and $C_1$ to $C_5$ alkyl groups such as methyl or ethyl are preferred, independently, for $R^5$, $R^6$, and $R^7$. More preferably, $R^5$, $R^6$, and $R^7$ are all H.

$Q^1$, $Q^2$, and $Q^3$ can all be nitrogen (N) in FORMULA B. In a preferred embodiment, not all of $Q^1$, $Q^2$, and $Q^3$ are the same, particularly for making waxes or polyethylenes. It is more preferred to have (a) N for $Q^1$, N for $Q^2$, and O for $Q^3$; or (b) O for $Q^1$, N for $Q^2$, and O for $Q^3$.

Preferably $Q^2$ is nitrogen (N). When $Q^1$ and $Q^2$ are both nitrogen, it is preferred that $Q^3$ is oxygen or sulfur, except for ethylene dimerization to high purity 1-butene or 2-butenes or mixtures thereof. In this case, $R^4$ does not exist (i.e. none) to satisfy the valence requirement of oxygen or sulfur. Ethylene can be dimerized to butene by using the present invention. For ethylene dimerization to 1-butene in excess of 98%, preferably in excess of 99% or higher purity among butene isomers, it is preferred to have $Q^1$, $Q^2$, and $Q^3$ all being nitrogen; and preferably $R^2$ and $R^4$ are phenyl and the corresponding $R^{11}$ is preferred to be independently selected from the group consisting of methyl, ethyl, n-propyl or isopropyl. For ethylene dimerization to butenes (1-butene, cic-2-butene, trans-2-butene mixture), it is preferred to have $Q^1$, $Q^2$, and $Q^3$ all being nitrogen; and preferably $R^2$ and $R^4$ are both phenyl and the corresponding two $R^{11}$ groups are preferably hydrogen. (see FORMULA C below)

Regardless which elements are selected for $Q^2$ and $Q^3$, it is preferred to have selected from $C_1$ to $C_5$ alkyl groups, 1-ring aryl and substituted aryl groups (i.e. phenyl groups) selected independently for $R^1$ and $R^3$. Methyl group is more preferred for both $R^1$ and $R^3$.

If either or both of $Q^2$ and $Q^3$ are nitrogen, then it is preferred to have phenyl groups for $R^2$ and/or $R^4$ attached to the nitrogen and the phenyl groups, selected independently for $Q^2$ and/or $Q^3$, are shown as follows (FORMULA C)

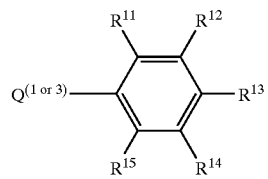

wherein $R^{11}$, $R^{12}$, $R^{13}$, $R^{14}$, and $R^{15}$ are individually selected from H, $C_1$ to $C_{20}$ alkyl groups, substituted $C_1$ to $C_{20}$ alkyl groups, 1–3 ring aryl groups, substituted 1–3 ring aryl groups, F, Cl, Br, I, amino groups, silyl groups such as $Si(CH_3)_3$, $Si(phenyl)_3$, and the like. Many other substituents such as nitro groups can also be used for making the metal-tridentate ligand complexes. However, if the complexes are used as catalysts for polymerization reactions, all of the above-mentioned R's should not have functional groups that would interfere with the polymerization reactions themselves or other components such as co-catalysts, if present. It is preferred to have H for $R^{12}$, $R^{13}$, and $R^{14}$. It is also preferable to have a $C_1$–$C_5$ alkyl group or H for either or both of $R^{11}$ and $R^{15}$. More preferred $R^{11}$ and $R^{15}$ are selected independently from the group consisting of H, methyl, ethyl, n-propyl, iso-propyl, and n-butyl groups. As already discussed, $Q^1$, $Q^2$ and $Q^3$ are preferably all nitrogen and only one of $R^{11}$ and $R^{15}$ is H when ethylene dimerization to 1-butene (in excess of 98%, or preferably in excess of 99% or even higher purity) is the preferred polymerization reaction. When 2-butenes or butene mixtures are the preferred ethylene dimerization products, both $R^{11}$ and $R^{15}$ are preferred to be H.

When the metal M is selected from the group consisting of manganese, chromium, vanadium, and mixtures thereof, it is preferred to have H, methyl, iso-propyl, and/or n-butyl groups for both $R^{11}$ and $R^{15}$ in order for the complexes to be better catalysts, particularly as catalysts for ethylene polymerization or co-polymerization in the presence of a co-catalyst such as aluminum alkyls, aluminum alkyl halides, alumoxanes such as MAO or MMAO (modified MAO, some are commercially available products from Akzo Nobel in heptane solutions.).

FORMULA B is a preferred embodiment of the present invention. As FORMULA A INDICATES, it is also within the scope of the present invention that a five-membered ring containing $Q^1$ may be used as part of the tridentate ligand. In this case, $R^7$ and the carbon to which it is attached in FORMULA B do not exist. It is still contemplated that the five-membered ring portion possesses aromatic characteristics. Depending on $Q^1$, the electrical (ionic) charge of the entire metal complex has to be balanced to zero with a proper number of "L's" present.

Another embodiment of the present invention provides a multidentate ligand with 2, 4, 5 or 6 coordinating atoms. While the three coordinating atoms in FORMULA B are more or less on the same plane, i.e. co-planar, this may not be the case for all of the coordinating atoms in a tetra-, penta-, or hexa-dentate ligand.

As already mentioned briefly, a preferred solvent includes, but is not limited to, coordinating solvents (i.e. Lewis base type solvents or electron pair donating solvents), particularly polar oxygenated solvents such as alcohols, ethers, esters, ketones, or mixtures. Some water may be present with the alcohols, ethers, glycols, or other water-miscible organic solvents. Examples of suitable polar oxygenated solvents include, but are not limited to, dimethyl ether, diethyl ether, methyl ethyl ether, monoethers or diethers of glycols such as dimethyl glycol ether, furans, dihydrofuran, substituted dihydrofurans, tetrahydrofuran (THF), tetrahydropyrans, (1,3 and/or 1,4-) dioxanes, methyl acetate, ethyl acetate, methyl ethyl ketone, acetone, and the like and mixtures thereof. Acyclic or cyclic polyethers such as poly(ethylene glycol) ethers, crown ethers (such as 12-crown-4 or 18-crown-6) and their mixtures can also be used even though some of them may be much more expensive than others.

THF is a more preferred solvent, particularly when $CrCl_2$ is used as a starting material with 6-[1-{(2,6-dimethylphenyl)imino}ethyl]-2-acetylpyridine and 6-[1-{(2,6-diisopropylphenyl)imino}ethyl]-2-acetylpyridine as the ligands. Other polar solvents such as 1,4-dioxane, tetrahydropyran, halogenated hydrocarbons (chloroform or dichloromethane), thioethers, and the like also may be used alone or as mixtures between themselves or with other solvents, particularly those disclosed herein.

The following general procedure may be used to prepare the metal complexes. A first amount of a metal starting material, such as a halide, and a second amount of a ligand, such as 6-[1-{(2,6-dimethylphenyl)imino}ethyl]-2-acetylpyridine are mixed in a suitable solvent under conditions effective to produce the product. The mixture is thoroughly mixed with proper agitation or gas purging for a period from one minute to 30 days. Then, optionally the mixture may be let stand for an additional one minute to thirty days without agitation. If the product is an insoluble solid in the reaction solvent, it is filtered and optionally washed with the same solvent or another solvent, preferably a more volatile one. The washed product is then placed under vacuum or in a flowing gas condition to remove all the volatiles. If the product is soluble in the reaction solvent under the conditions, one can either remove part or all of the solvent, and/or cool the reaction mixture to a lower temperature to precipitate the product solid followed by filtration and optional washing. The solid can also be recovered by removing the solvent by other techniques such decantation known to those skilled in the art. The product is then weighed to determine yield and characterized by chemical analyses, NMR and/or ICP to determine its chemical composition and structure. In the rare event that the complex is a liquid at room temperature, the product can be recovered or purified by distillation, chromatography or other means known in the art.

As shown in FORMULA B, it is most likely that the metal-tridentate ligand complex has a ligand to metal molar ratio of 1:1. For preparation of the complex, the molar ratio of the ligand to the metal (whatever the starting material may be) should be in the range of 1:10 to 10:1; preferably 1:5 to 5:1; more preferably 1:2 to 2:1. Availability, costs, desired product, and product separation/purification are the major factors to be considered for selecting a suitable molar ratio.

The complex formation reaction can be carried out at a temperature in the range of from about −20° C. to about 150° C., preferably form about 0° C. to about 90° C., and more preferably from about 15° C. to about 50° C. The pressure is normally not a critical factor. It is convenient to use ambient pressure, but sub- or super-atmospheric pressures may be used. Some of the starting materials and/or products may be air and/or moisture sensitive. It is therefore preferred to carry out the reaction and/or the product recovery and/or the product purification steps in a dried atmosphere such as nitrogen, argon, helium, neon, krypton, methane, ethane, propane, and mixtures thereof. If there are no other concerns, air, carbon monoxide, carbon dioxide, hydrogen may also be used individually, or as mixtures thereof, or as mixtures with inert gases or other gases. It may also be easier to keep moisture and oxygen out by having a reactor or reaction system pressure slightly higher than the ambient (atmospheric) pressure.

If it is desirable to support the metal complex on a carrier, there are many inorganic and/or organic carriers within the scope of the present invention. The selection depends on the nature of the metal complex, the co-catalyst if any, the desired polymerization reaction and other similar factors. It is preferred that the support provide some benefits to the catalyst system chemically or catalytically, but this is not required. There may be other reasons to select a particular support, for instance easier product purification, lower cost, cheaper manufacturing process, etc. Inorganic carriers suitable for the present invention include, but are not limited to, crystalline or amorphous silicas (including those disclosed in U.S. Pat. No. 6,107,236), crystalline or amorphous aluminas, zeolites (both natural and synthetic ones such as ZSM-5, ZSM-11, etc), crystalline or amorphous silicoaluminas, silicoaluiminophosphates (SAPOs), metalaluminophosphates (MEAPOs), aluminophosphates (ALPOs), titanium oxide (titania), zirconium oxide (zirconia), magnesium oxide, magnesium chloride, manganese chloride, and the like and mixtures thereof. Some typical examples of suitable supports can be found in "Heterogeneous single site catalysts for olefin polymerization" Gregory G. Hlatky, *Chemical Reviews*, 100, pp 1347–1376 (2000).

A metal-multidentate ligand complex may be placed on the supports by a number of known methods. The support can be present during or after the metal complex is made from the starting materials. Non-limiting examples include incipient wetness, in-situ mixing, solution impregnation, dry-mixing/admixing/blending, ion-exchange, sublimation, co-precipitation, and combinations and/or repetitions thereof.

As already mentioned hereinabove, the present invention also relates to a novel multi-component catalyst system for olefin, particularly ethylene or propylene or mixtures thereof, polymerization process. This multi-component catalyst system comprises (a) at least one first component consisting essentially of one or more ethylene or propylene dimerization and/or trimerization catalyst comprising the metal-multidentate ligand complexes, particularly the chromium based complexes as described herein (such as those encompassed by FORMULA B) and preferably all coordinating sites are nitrogen; and (b) at least one second component consisting essentially of an olefin polymerization catalyst selected from the group consisting of Ziegler-Natta catalyst, its precursor, a metallocene or metallocene precursor, a second metal-tridentate ligand complex wherein it is different from the one(s) used in (a) and/or not all three coordinating sites are the same, and mixtures thereof. This catalyst system, supported or unsupported, may be used preferably with a co-catalyst containing at least one organometallic compound as disclosed herein to polymerize olefins, particularly α-olefins like ethylene or propylene or mixtures of ethylene and propylene to a product. The product may be wax, PE, PP, LDPE, LLDPE, and the like, and mixtures thereof. Without being bound by a particular theory, it is expected that the first component will dimerize or trimerize ethylene and/or propylene to butene, pentene, hexane, heptane, octane and/or nonene. These olefins serve as co-monomers during polymerization of ethylene and/or propylene catalyzed by the second component. Of course, it is also expected that oligomerization of these $C_4$–$C_9$ olefins with or without additional ethylene and/or propylene incorporated can also take place. Depending on the catalyst system and reaction conditions selected, products of various characteristics can be produced in accordance with the disclosures of the present invention.

Examples of suitable ethylene and/or propylene dimerization an-d/or trimerization catalyst include, but are not limited to, those comprising a metal-tridentate ligand complex such as those represented by FORMULA B, wherein preferably the metal is selected from the group consisting of Cr, V, Mn, Ni, and/or mixtures thereof. It is more preferred that the metal M is or consists essentially of chromium (Cr), $Q^1$, $Q^2$, and $Q^3$ are all nitrogen (N), both $R^2$ and $R^4$ have the structure of FORMULA C (i.e. phenyl groups), $R^{11}$ is preferably selected from H, methyl, ethyl, n-propyl, iso-propyl, and n-butyl groups, and $R^{15}$ is H.

Examples of suitable Ziegler or Ziegler-Natta type catalysts for the second component include, but are not limited to those disclosed in Gregory G. Hlatky, *Chemical Reviews*, 100, pp 1347–1376 (2000). The catalysts can be either "metallocene" or "non-metallocene" type. Some examples can be found in Gibson et al, Angew. Chem. Int'l Ed., 38, 428 (1999); and Pullkat et al, Catal. Rev. —Sci. Eng., 41(3&4), 389–428 (1999).

Examples of metallocenes or metallocene precursors suitable for use as the second component of the multi-component catalyst system include, but are not limited to those based on cyclopentadienyl or modified cyclopentadienyl ligands. Non-liming examples can be found in many publications such as Waymouth et al, Chemical Reviews, 98, 2587–2598 (1998); Alt et al, J. Mol. Cat. A: Chemical 165, 23–32 (2001); Alt et al, Chem. Rev., 100, 1205–1222 (2000); and Ittel et al, Chem. Rev., 100, 1169–1204 (2000).

The metal-ligand complex of the present invention as disclosed herein with or without a support can be used to effect polymerization of olefins, particularly in the presence of a co-catalyst. It should be repeated again that, as already defined earlier, the term polymerization is used herein broadly to include dimerization, trimerization, and/or oligomerization. Thus, the products could be dimers, trimers, oligomers (some of them are described herein as wax or waxes which contain about twenty to about sixty or more carbons), polymers and/or mixtures thereof. Under suitable conditions, the products obtained are characterized by having a Schulz-Flory constant (K) in the range of from about 0.4 to about 0.98, preferably from about 0.5 to about 0.9, more preferably from about 0.55 to about 0.8.

The multi-component catalyst system is also useful in polymerizing olefins, particularly lower alpha-olefins in the presence of an organometallic co-catalyst. While not bound by a particular theory, it is believed that the ethylene and/or propylene dimers and or trimers produced by the first component are incorporated as co-monomer(s) into the polymer products produced by a co-polymerization catalyzed by the second component polymerization catalyst. The second component can be mixed with the first component followed by contacting with a suitable co-catalyst; or the second component can be added, with or without additional co-catalyst, to the polymerization reactor after some initial reaction (such as ethylene or propylene dimerization reaction) has already taken place. When the multi-component catalyst is used and the olefin is selected from ethylene and propylene, the product is usually characterized by being a polyethylene (PE), low-density polyethylene (LDPE), linear low density polyethylene (LLDPE), polypropylene (PP), waxes, and the like, and mixtures thereof. The products are particularly characterized by having branching along the polymer chain. Such branching may be identified or characterized by nuclear magnetic resonance (NMR), gas chromatography (GC), thermal properties, or many other methods known to one skilled in art, which are used to characterize co-polymers.

For most polymerization reactions, co-catalysts are used for supported, unsupported metal complexes or mixtures thereof. Many co-catalysts can be used for the present invention to activate the catalyst or to provide better polymerization activity/selectivity or other properties. Suitable co-catalysts include, but are not limited to organometallic compounds (monomeric or oligomeric metal alkyls, metal aryls, metal alkyl-aryls, with or without other moieties such as halide or alkoxide) comprising at least one of the metals selected from the group consisting of B, Al, Ga, Be, Mg, Ca, Sr, Ba, Li, Na, K, Rb, Cs, Zn, Cd, and Sn. These are referred to as organoboron, organoaluminum, organogallium, organoberyllium, organomagnesiu, organocalcium, organostrontium, organobarium, organolithium, organosodium, organopotassium, organorubidium, organocesium, organozinc, organocadmium and organotin compounds respectively. The only requirement in these compounds is that there is at least one carbon-metal bond like alkyl-M, aryl-M, and delocalized carbon-containing moiety (for instance a cyclopentadienyl group, $C_5H_5^-$)-M bond. As it will become clear later, there may be other groups such as halide, alkoxide and other similar groups. There also may be more than one metal atom in these organometallic compounds. A general character is that they are active enough to reduce the oxidation states of the metals in the metal-tridentate complex, or metallocene precursor, or Ziegler catalyst precursor, or Ziegler-Natta catalyst precursors. Preferred examples of suitable co-catalysts include, but are not limited to organoaluminum compounds (such as aluminum alkyl compounds, with or without halides, alkoxides or other ligands or moieties), organoboron compounds, organolithium compounds, organotin compounds, and mixtures or solutions (many commercial materials are in solvents such as alkanes or alcohols) thereof. Organoaluminum compounds in all forms are more preferred for their chemical properties, physical properties, commercial availability, and costs.

More specific and preferred, but non-limiting, examples are trimethylaluminum, triethylaluminum, diethylaluminum chloride, diethylaluminum ethoxide, diethylaluminum cyanide, diisobutylaluminum chloride, triisobutylaluminum, t-butyl alumoxanes, ethylaluminum sesquichloride, alumoxanes such as MAO (methylalumoxane), modified methylalumoxane (MAO which contains other aluminum alkyl species or moieties), dimethylboron bromide, methylboron dibromide, tributylboron, tributyltin chloride, tetra-n-propyltin, tetra-n-butyltin, and mixtures thereof. These materials can be purchased from commercial sources or prepared in accordance with published methods that are known to those skilled in the art. As already mentioned, these materials, particularly those purchased from commercial sources, may further contain solvents like toluene, hexane, alcohols, etc. These solvents generally do not interfere with the olefin polymerization reactions of this invention.

The relative amount of a co-catalyst to a catalyst is the range of from about 10,000:1 to about 1:10,000, preferably from about 5,000:1 to about 1:5,000, more preferably from about 2,000:1 to about 1:2,000, all being molar ratios. In the case of the multi-component catalyst system, the relative amount of the first component to the second component is in the range of from about 0.001:1 to about 1:0.001; preferably 0.01:1 to 1:0.01; more preferably from 0.1:1 to 1:0.1; all being molar basis. The relative amount of a co-catalyst to the total amount catalyst in the multi-component catalyst system is the range of from about 10,000:1 to about 1:10,000, preferably from about 5,000:1 to about 1:5,000, more preferably from about 2,000:1 to about 1:2,000, all being molar ratios.

The co-catalyst(s) can be added to the metal-bidentate, -tridentate, or multi-dentate complexes (catalyst) in any manner known in the art. For instance, the catalyst and the co-catalyst can be mixed first before bringing in contact with a feed comprising an olefin or an olefin mixture. In the alternative, the co-catalyst can be mixed with the olefin-containing feed first before this mixture is mixed with the metal-ligand complex catalyst. Many other modifications are possible. As already described above, in a multi-component catalyst system, the second component, with or without additional co-catalyst, may be pre-mixed with the first component, or it can be added to the reactor after some or all of the initial dimerization and/or trimerization reaction of ethylene and/or propylene is completed.

Many different olefins can be polymerized or co-polymerized (including dimerization, co-dimerization, trimerization, co-trimerization, other oligomerizations or co-oligomerizations) using the catalyst system of this invention and all these are within the scope of this invention. Examples include, but are not limited to ethylene, propylene, 1-butene, cis-2-butene, trans-2-butene, butadiene, isoprene, 1,3-pentadiene, 1,4-pentadiene, 1,3-hexadiene, 1,4-hexadiene, 1,5-hexadiene, 4-vinylcyclohexene, norbornadiene, ethylidenenorbornene, vinylnorbornene, $C_5$ and higher olefins such as 1-petene, 3-methyl-1-pentene, 4-methyl-1-pentene, 1-hexene, 1-heptene, 1-octene, 1-nonene, 1-decene, 1-undecene, 1-dodecene, 1-octadecene, cyclopentene, methylcyclopentene (1-, or 2-, or 3- and mixtures), vinylcyclohexane, norbornene, vinyl aromatics such as styrene, o-methylstyrene, m-methylstyrene, p-methylstyrene, α-methylstyrene, p-ethylstyrene, p-t-butylstyrene, divinylbenzene, 1-vinylnaphthalene, 2-vinylnaphthalene, 2-vinylpyridiene, 3-vinylpyridine, 4-vinylpyridine, and the like, and mixtures thereof.

The product of the polymerization reaction most often comprises (co-) dimers to polymers, depending on the catalyst, the co-catalyst if any, the feed and other reaction conditions. In a preferred embodiment of this invention, the product comprises primarily terminal (i.e. α-) olefin products, linear or branched or mixtures thereof. The distribution of various compounds in the product depends on the reaction conditions, feed composition as well as the catalyst, including co-catalyst. It is preferred to have narrow distribution of products, particularly for dimerization and trimerization reactions. Product separation and purification will be easier if there are fewer compounds in the product. For ethylene dimerization reactions, a typical product contains primarily 1-butene. It is preferable to have 1-butene in excess of 98% among the butene isomers. It is more preferable to have 1-butene of 99% or higher purity among the butene isomers.

The polymerization process or reaction, as previously defined to include (co-) dimerization, (co-)trimerization or other oligomerizations of one or more olefins, may be carried out in any suitable mode or physical form. For example, the reaction can be homogeneous, heterogeneous or a combination thereof. The polymerization process may be carried out in a slurry phase, gas phase, liquid phase, super-critical phase, or the like, and combinations thereof. The polymerization can be carried out in a batch mode, continuous mode, semi-continuous mode or any other manners known to one skilled in the technology.

Because of the reactivity of metal-multidentate ligand complex and/or the co-catalyst used for the polymerization reaction or for other considerations, it is generally preferred to carry out in a non-reactive or inert atmosphere the reactions—complex preparation and recovery/purification (if any), activation, olefin polymerization, or post polymerization treatments (such as to deactivate the entire catalyst system or product recovery/purification). Sometimes it is also preferred to have some hydrogen in the system. Certainly, if the products or the reaction systems are not affected by oxygen and/or water and there are no other safety concerns under the reaction conditions, then it is more convenient and cost effective to carry out certain individual steps in air.

The polymerization reaction was carried out in a suitable reactor under conditions effective to produce the desired product. The important reaction parameters include, but are not limited to, the metal-multidentate ligand complex, the metallocene and/or metallocene precursor if used, the co-catalyst, ratio of co-catalyst to the catalyst, the feed, the medium (i.e. solvent) if one is used, reaction temperature, reaction time, olefin partial pressure if it is a gas or has a substantial vapor pressure under the reaction condition, replenishment of consumed olefin if desirable, amount of co-monomer if present, other reactants such as hydrogen desired, reactive impurities (such as oxygen and water) in the reaction system, and the product work-up procedure.

If the olefin monomer is a gas under the conditions, such as ethylene, then a suitable partial pressure is in the range of from about 0.1 psia (0.7 kPa) to about 2,500 psia (17,250 kPa), preferably 0.2 psia (1.4 kPa) to 2,000 psia (13,800 kPa), more preferably from 0.5 psia (3.4 kPa) to 1,500 psia (10,300 kPa) Because the total system pressure will decrease as the gaseous olefin(s) is(are) polymerized or consumed, one can continue to add more monomer(s) to the reactor at a set rate (such as a continuous flow of the monomer to the reactor), add different monomers, if more than one, at different rates, add more monomer(s) on demand to maintain a certain system pressure, add a second different monomer or monomer mixtures to the reactor, let the system pressure decrease, any other choices known to those skilled in the art, or a combination thereof. If no additional monomer is needed or desired, gases inert to the reaction mixture may be used to make the necessary pressure.

The polymerization temperature is in the range of from about 0° C. to about 150° C., preferably from about 10° C. to about 120° C., more preferably from 20° C. to 75° C. A suitable temperature is determined by a number of factors, such as catalyst stability, catalyst activity, the monomer or monomers to be polymerized or co-polymerized, the properties of the co-catalyst, and others.

The olefin monomer(s) may be pre-mixed or added simultaneously to the polymerization reactor, or added sequentially to the reactor or metered into the reactor in some other manner. The olefin monomer(s) can also be added as needed (on demand) to maintain a certain system pressure. The olefin monomer(s) can also be added continuously at certain rate. Or, the olefin monomers can also be added at the beginning and then let them be consumed without any additions. All these may be done at fixed reaction parameters or variable parameters such as pressure ramp or temperature ramp. Combinations of some of these may also be used.

The olefin monomer(s), the metal-ligand complex or the multi-component catalyst system, the co-catalyst (if used), and any other materials, such as a medium, may be mixed or contacted with one another according to the sequences or orders known to those skilled in the art. Certainly, the first component, the second component, and other components (if any) and the co-catalyst may be brought into contact with one another in any order or sequence or simultaneously.

The following examples illustrate preparations of exemplary ligands, preparations of certain metal-multidentate ligand complexes, and polymerization of olefins by using catalysts comprising the complexes and co-catalyst, and analyses used to characterize different products from these reactions.

EXAMPLE 1

This example shows a typical preparation method of a tridentate ligand like 6-[1-{(2,6-dimethylphenyl)imino}ethyl]-2-acetylpyridine. 3.0 g (18.4 mmol) of 2,6-diacetylpyridine and 2.3 ml (18.7 mmol) of 2,6-dimethyl aniline were added to a flask with a stirbar and 20 ml of anhydrous methanol. Several drops of glacial acetic acid were added, and the reaction was heated with stirring for 3 days at 55° C. The reaction flask was then placed in a freezer at −20° C., resulting in the formation of yellow, needlelike crystals. These crystals were removed by filtration and washed with cold methanol (yield=1.15 g, 23.5%).

EXAMPLE 2

The following is one example of demonstrating how a chromium based complex—chromium(II) 6-[1-{(2,6-diisopropylphenyl)imino}ethyl]-2-acetylpyridine chloride (with THF) was prepared:

A sample of 1.0 gram of 6-[1-{(2,6-diisopropylphenyl)imino}ethyl]-2-acetylpyridine and 382 mg of chromium chloride ($CrCl_2$, obtained from Aldrich Chemical Company) were transferred into a flask in a drybox under argon. Anhydrous tetrahyfuran (THF), about 50 ml, was added to this mixture. The mixture was stirred overnight under argon. The mixture was then allowed to stand for three days, followed by addition of about 100 ml of n-pentane. A grayish purple solid was isolated by filtration in air. The filtrate was green. The recovered solid was further washed with n-pentane and dried. Total yield was 1.237 grams (90% of theoretical yield).

This metal complex was used for the polymerization reaction Entry 9 and Entry 13 in TABLE I.

EXAMPLE 3

A similar method was used successfully to prepare a chromium(II) chloride complex containing 6-[1-{(2,6-dimethylphenyl)imino}ethyl]-2-acetylpyridine. The complex had a light purple color. The amount of tridentate ligand used was 267 mg and $CrCl_2$, 120 mg, was obtained from Strem Chemical Company.

This metal complex was used for the polymerization reaction Entry 8 in TABLE I.

EXAMPLE 4

The polymerization reactions were carried out in the following manner. All of the solvents such as anhydrous THF, heptane and cyclohexane were purchased from Aldrich Chemical Company and stored over molecular sieves before use. 1-hexene was obtained as a commercial grade of Chevron Phillips' NAO's and dried over molecular sieves. MMAO-3A was purchased from Akzo Nobel.

For small, low-pressure ethylene polymerization reactions, in an inert, oxygen and moisture free, atmosphere (such as a dry box filled with nitrogen or argon) the metal-ligand complex, such as a chromium-tridentate ligand complex, a medium (polymerization solvent) if one was used, and a stir-bar were placed in a flask. For a multi-component catalyst system, the second component was also added to the flask at the same time in the experiments. As already pointed out earlier, the second component also may be added later to a reactor with or without using additional co-catalyst such as aluminum alkyls. The flask was transferred to a Schlenk manifold and placed under a continuous ethylene purge. The flask contents were stirred rapidly for several minutes to saturate the solvent (such as heptane) with ethylene and to break apart any small chunks of the complex. A co-catalyst such as MMAO-3A from Akzo Nobel was added via a syringe while the stirring continued. Optionally, a cooling bath could be used to control and/or maintain the desired reaction temperature. For reactions in which light olefins (such as butenes) were the primary products, ethylene was continuously purged through and out of the reaction flask. For the reactions waxes and/or higher molecular weight polyethylenes (PE) were produced, ethylene was added "on demand."

For reactions carried out at a pressure higher than about ambient pressure, a one-liter Zipperclave™ reactor fro Autoclave Engineers was used. The reactor should be clean and dried appropriately. The metal-ligand complex was dissolved in a small amount of solvent such as methylene chloride in a breakable thin-glass tube, which was then bound to the stirrer shaft of the reactor. The reactor was then evacuated, charged with a medium if one used and a co-monomer if one is used, and a co-catalyst. If the co-monomer is a gas under ambient conditions, it would be added via a gas inlet. The olefin (such as ethylene) was then added and the stirred shaft was started, thus breaking the breakable thin-glass tube, thus contacting the metal-ligand complex with the co-catalyst and the olefin. For olefins such as ethylene, propylene or butene which are gases under ambient conditions, they were added through an inlet tube. It was preferred, particularly for ethylene. that the olefin was added "on demand," i.e. added enough to maintain a certain pre-determined pressure or pressure profile. The reactor temperature was maintained by passing a coolant through and cooling coil inside the reactor. After the desired reaction period was reached, it was more convenient to add a deactivating agent to "kill" the catalyst system for product work-up. For most reactions, and particularly when organoaluminum such as MAO or MMAO co-catalysts were used, an acidified methanol solution was used for this purpose. The product mixtures were then removed from the reactor, followed by filtration, washing or other common product purification techniques. The products were analyzed by gas chromatography (GC) and other analytic techniques or methods known to those skilled in the art.

Results from such polymerization reactions are shown in TABLE I. All of the catalysts contained chromium, and MMAO was used as the co-catalyst. $Q^1$ is nitrogen. $Q^2$ and $Q^3$ were both nitrogen for Type 1; $Q^2$ was nitrogen and $Q^3$ was oxygen for Type 2. $R^1$ and $R^3$ (when present in Type 1) were represented by FORMULA C with $R^{11}$ and $R^{15}$ shown in the Table. The reactions were carried out at temperatures between 25° C. (ambient temperature) and 100° C. Ethylene pressure was in the range of from 15 psia (100 kPa) to 415 psia (2,860 kPa).

Results from polymerizations using a multi-component catalyst system are shown in TABLE II. Unless otherwise specified, the designations and abbreviations are used to indicate the same. See more detailed descriptions of the two entries below. The metallocene precursor $C_5(CH_3)_4Si(CH_3)_2N(t\text{-}Bu)TiCl_2$ was prepared according to the method in literature

TABLE I

Polymerization of Ethylene and α-Olefins Using Chromium-Tridentate Ligand Complexes

| Entry | Type[a] | $R^{11}$ | $R^{15}$ | Complex amount (mg) | Al:Cr[c] | $P_{ethylene}$ (psi), comonomer (amount)[d] | Solvent (medium) (ml)[e] | Rxn length (min) | T (° C.) | Yield (g) | Prod.[f] (g/g Cr complex) | Notes |
|---|---|---|---|---|---|---|---|---|---|---|---|---|
| 1 | 1 | H | H | 5.7 | 500 | 15 | CyH(40) | 30 | 35 | n.d. | n.d. | rapid exotherm; mostly butene, heavily isomerized to c-and t-2-butene |
| 2 | 1 | Me | H | 6.1 | 400 | 15 | CyH(40) | 60 | 35 | nd. | n.d. | rapid exotherm, required cooling; mostly 1-butene, 99% purity |
| 3 | 1 | Et | H | 5.4 | 500 | 15 | CyH(40) | 80 | 35 | n.d. | n.d. | rapid exotherm, 99% pure 1-butene |
| 4 | 1 | iPr | H | 4.6 | 500 | 15 | CyH(40) | 30 | 35 | n.d. | n.d. | rapid exotherm, 99% pure 1-butene, small amts. of higher olefins |
| 5 | 1 | t-Bu | H | 5.2 | 500 | 15 | CyH(40) | 180 | 25 | 1.9 | 370 | major product is PE |
| 6 | 1 | Me | Me | 6.7 | 500 | 15 | CyH(40) | 120 | 35 | 10.4 | 1550 | $C_{max}$(GC)~$C_{48}$; Schulz Flory constant~0.96 |
| 7 | 1 | Me | H | 5.1 | 1100 | 400 | CyH(200) | 30 | 85 | n.d. | n.d. | very rapid exotherm, 99.6% 1-butene purity, small amt of hexenes, octenes, PE |
| 8 | 2 | Me | Me | 18.0 | 160 | 15 | heptane(50) | 180 | 25 | 6.0 | 330 | waxes |
| 9 | 2 | iPr | iPr | 21.0 | 120 | 15 | heptane(50) | 180 | 25 | 1.2 | 60 | heavy waxes |
| 10 | 2 | t-Bu | H | 6.3 | 500 | 15 | heptane(40) | 60 | 25 | 1.1 | 180 | heavy waxes/PE |
| 11 | 2 | Me | Me | 5.0 | 1150 | 400 | heptane(200) | 60 | 80 | 101 | 20,200 | α-olefin waxes, Schulz-Flory K~0.87 |
| 12 | 2 | Me | Me | 4.0 | 1150 | 400 | heptane(200) | 60 | 100 | 95 | 23,800 | α-olefin waxes, K~0.87 |
| 13 | 2 | iPr | iPr | 15.0 | 225 | 400 | heptane(200) | 120 | 60 | 25.0 | 1670 | heavy waxes, Mn = 750 |
| 14 | 2 | Me | Me | 14.6 | 160 | 15, 1-hexene (50 ml) | n.a. | 360 | 25 | 1.8 | 100 | gummy solid; significant $C_6$ incorp. by GC |
| 15 | 2 | Me | Me | 13.6 | 260 | 15, 1-hexene (9 ml) | heptane(45) | 180 | 25 | 22.2 | 1520 | waxes; significant $C_6$ incorp. by GC |
| 16 | 2 | Me | M | 13.6 | 260 | 15, 1-octadecene (15 ml) | Heptane(50) | 1200 | 25 | 35.5 | 2610 | Waxes Significant $C_{18}$ incorporated |

Notes:
[a]Type 1: $Q^1$, $Q^2$, and $Q^3$ are all nitrogen; Type 2, $Q^i$ and $Q^2$ are nitrogen, and $Q^3$ is oxygen; $R^1$ and $R^3$ (if present) are represented by FORMULA C.
[b]For example, 2-H represents unsubstituted aryl rings for a Type 1 complex.
[c]Molar ratio of Al to Cr in the reaction.
[d]Ethylene pressure, and amount of comonomer present (if applicable).
[e]CyH is cyclohexane.
[f]Prod. = productivity, which was not determined for reactions in which the major product was butene.

TABLE II

| Entry | 17 | 18 |
|---|---|---|
| Type (First Component) | 1 | 1 |
| $R^{11}$ | Me | IPr |
| $R^{15}$ | H | H |
| Amount (mg) | 2.5 | 2.0 |
| Al:Cr | 2000 | 3000 |
| Second Component | g | 2 |
| $R^{11}$ | — | Me |
| $R^{15}$ | — | Me |
| Amount (mg) | 4.0 | 7.5 |
| Al:Metal | 1000 | 600 |
| $P_{ethylene}$ (psia) | 15 | 15 |
| Solvent, or medium (ml) | Heptane (40) | Heptane (50) |
| Reaction time (min) | 60 | 240 |
| T (° C.) | 30–35 | 25 |
| Yield (g) | 3.61 | 1.62 |
| Productivity (g/g Cr complex) | 900 | 170 |
| Notes | PE Branching observed[h] | PE Branching observed[h] |

[g]$C_5(CH_3)_4Si(CH_3)_2N(t\text{-}Bu)TiCl_2$
[h]The branching, observed from gas chromatographic analyses is similar to Entry 15, where 1-hexene was used as a co-monomer.

For Entry 1, where both $R^{11}$ and $R^{15}$ are hydrogen (H), the butene product contains substantial amount of cis- and trans-2-butenes. For Entry 14, there was substantial incorporation of 1-hexene in the products by analyses. For Entry 15, there was substantial incorporation of 1-hexene in the products by analyses. For Entry 11, K was about 0.87. For Entry 12, K was also about 0.87. For Entry 2, in the $C_4$ olefins, 1-butene was in excess of 99% purity among the butene isomers; some low purity of $C_6$ products. For Entry 7, in the $C_4$ olefins, 1-butene was about 99.6% pure; in the $C_6$ olefins, 1-hexene was about 93% pure. Entry 3 and Entry 4 also gave 1-butene at 99% purity. Entry 16 showed the incorporation of 1-$C_{18}$ olefin.

It can be seen from these results that a catalyst comprising the chromium metal complexes and an aluminum alkyl co-catalyst, MMAO, were effective in both polymerization and co-polymerization. Products comprising high α-olefin concentrations (such as 1-butene and 1-hexene) were produced when all three coordinating sites are nitrogen and there was a single ortho-substitution of on the phenyl ring as represented by FORMULA C. When the ortho-substitution was a large t-butyl group, polyethylene was produced.

Results in TABLE I also showed that catalysts comprising the chromium metal complexes and a suitable aluminum alkyl, MMAO, were very active, having good productivity per gram of chromium.

Entry 17 in TABLE II shows that when a chromium tridentate ligand (type 1, all three coordinating sites were nitrogen) complex was used in combination with a metallocene precursor, polyethylene (wax type) was obtained with ethylene as the feed. The product was very similar to that obtained in Entry 15, where 1-hexene was used as a co-monomer. GC analysis showed branching on the polymer chains.

Entry 18 in TABLE II shows that when a chromium tridentate ligand (all three coordinating sites were nitrogen) complex was used in combination with a different chromium tridentate ligand (type 2, $Q^1$ and $Q^2$ were nitrogen, $Q^3$, oxygen) complex, polyethylene (wax type) was obtained with ethylene alone. The product was very similar to that obtained in Entry 15, where 1-hexene was used as a co-monomer. GC analysis showed branching on the polymer chains.

The examples herein are provided only for the purpose of illustrating the embodied invention. They are not intended and should not be treated as to limit the spirit and scope of the instant invention, which is defined solely by the specification and claims.

What is claimed is:

1. A metal-tridentate ligand complex comprising a structure of FORMULA B:

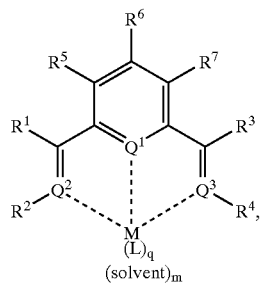

wherein
$Q^1$, $Q^2$, and $Q^3$; independently selected from O, S, N, and P;
$R^1$ and $R^3$; independently selected from H, $C_1$ to $C_{20}$ alkyl groups 1-, 2- or 3-ring aryl groups and substituted aryl groups;
$R^2$ and $R^4$; if $Q^2$ or $Q^3$ is O or S, none,
if $Q^2$ or $Q^3$ is either N or P, independently selected from H, $C_1$ $C_{20}$ alkyl groups, 1-, 2- or 3-ring aryl groups and substituted aryl groups;
$R^5$, $R^6$, and $R^7$; independently selected from H, $C_1$ to $C_{20}$ alkyl groups;
M: a first transition metal selected from the group consisting of Cr, Mn, V, Ni, Ti, Zr, Hf, Ta, and mixtures thereof;
L: each L independently selected from the group consisting of F, Cl, Br, I, $C_1$ to $C_{20}$ alkyl, $C_5$ to $C_{14}$ aryl nitrate, $OR^{21}$, $OC(=O)R^{22}$; $R^{23}$; SCN, CO, H, wherein $R^{21}$, $R^{22}$, and $R^{23}$ are independently selected from the group consisting of H, $C_1$ to $C_{20}$ alkyl groups substituted alkyl group 1-, 2- or 3-ring aryl groups, substituted aryl groups and silyl groups;
solvent: selected from the group consisting of ethers, polyethers, esters, alcohols, halogenated hydrocarbons and mixtures thereof;
q: 0–5 (integer) to balance overall electrical charge; and
m: 0–10 (integer or fractional).

2. The metal-tridentate ligand complex of claim 1, wherein $Q^1$ and $Q^2$ are nitrogen, $Q^3$ is oxygen, and $R^4$ does not exist.

3. The metal-tridentate ligand complex of claim 2, wherein $R^2$ has a structure of FORMULA C:

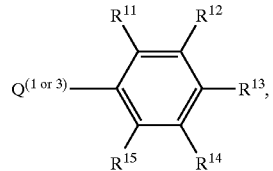

wherein $R^{11}$, $R^{12}$, $R^{13}$, $R^{14}$, and $R^{15}$ are individually selected from H, $C_1$ to $C_{20}$ alkyl groups, substituted $C_1$ to $C_{20}$ alkyl groups, 1–3 ring aryl groups, substituted 1–3 ring aryl groups, F, Cl, Br, I, amino groups, silyl groups such as $Si(CH_3)_3$, Si(phenyl), and the like.

4. The metal-tridentate ligand complex of claim 3, wherein
$R^1$ and $R^3$ are independently selected from the group consisting of $C_1$ to $C_5$ alkyls;
$R^{12}$, $R^{13}$, and $R^{14}$ are H; and
$R^{11}$ and $R^{15}$ are selected independently from the group consisting of H, methyl, ethyl, n-propyl, and iso-propyl groups.

5. The metal-tridentate ligand complex of claim 4, wherein M consists essentially of an element selected from the group consisting of, chromium, vanadium, manganese, and mixtures thereof.

6. The metal-tridentate ligand complex of claim 1, wherein
M consists essentially of an element selected from the group consisting of chromium, vanadium, manganese and mixtures thereof;
$Q^1$ and $Q^2$ are nitrogen, $Q^3$ is oxygen, and $R^4$ does not exist;
$R^2$ is selected from the group consisting of $C_1$ to $C_5$ alkyl groups, 1–3 ring aryl groups;
$R^5$ $R^6$, and $R^7$ are independently selected from H, and $C_1$ to $C_5$ alkyl groups;
each L is independently selected from F, Cl, Br, I, alkyl, aryl, and mixtures thereof; and
the solvent is selected from the group consisting of ether, ester, alcohol, and mixtures thereof.

7. The metal-tridentate ligand complex of claim 6, wherein,
M consists essentially of chromium;
q is 2;
L is chloride;
$R^2$ has a structure of FORMULA C:

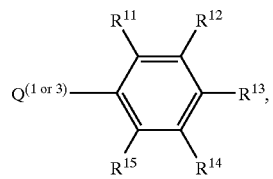

wherein
$R^{12}$ $R^{13}$, and $R^{14}$ are H; and
$R^{11}$ and $R^{15}$ are selected independently from the group consisting of H, methyl, ethyl, n-propyl, and iso-propyl groups.

8. A method for preparing the metal-tridentate ligand complex of claim 1, the method comprises:

contacting a first component comprising metal (M) with a second component comprising a tridentate ligand with a structure of FORMULA A:

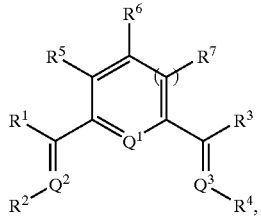

wherein $Q^1$, $Q^2$, $Q^3$; independently selected from O, S, N, and P;

$R^1$ and $R^3$; independently selected from H, $C_1$ to $C_{20}$ alkyl groups, 1-, 2- or 3-ring aryl groups and substituted aryl groups;

$R^2$ and $R^4$; if $Q^2$ or $Q^3$ is O or S, none,
if $Q^2$ $Q^3$ is either N or P, independently selected from H, $C_1$ to $C_{20}$ alkyl groups, 1-, 2- or 3-ring aryl groups and substituted aryl groups; and $R^5$, $R^6$, and $R^7$; independently selected from H, $C_1$ to $C_{20}$ alkyl groups and $R^7$ does not exist if the carbon to which it is attached is not present;

reacting the first component with the second component under conditions effective to produce the metal-tridentate ligand complex; and recovering the metal-tridentate ligand complex.

9. The method of claim 8, wherein

M consists essentially of an element selected from the group consisting of chromium, vanadium, manganese, and mixtures thereof;

$Q^1$ and $Q^2$ are nitrogen, $Q^3$ is oxygen, and $R^4$ does not exist;

$R^1$ and $R^3$ are independently selected from $C_1$ to $C_5$ alkyl groups;

$R^2$ has a structure of FORMULA C:

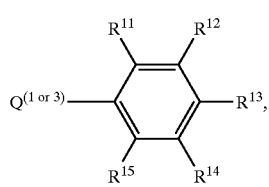

wherein $R^{12}$, $R^{11}$, and $R^{14}$ are H, and $R^{11}$ and $R^{15}$ are independently selected from the group consisting of H, methyl, and iso-propyl groups;

$R^5$ $R^6$, and $R^7$ are independently selected from H, and $C_1$ to $C_5$ alkyl groups; and each L is independently selected from F, Cl, Br, I, alkyl, aryl, and mixtures thereof.

10. A catalyst system for polymerizing at least one olefin to form a product the catalyst system comprises a metal-tridentate ligand complex having FORMULA B:

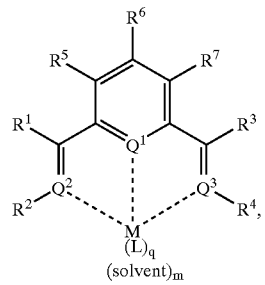

wherein $Q^1$, $Q^2$, and $Q^3$; independently selected from O, S, N, and P;

$R^1$ and $R^3$; independently selected from H, $C_1$ to $C_{20}$ alkyl groups, 1-, 2- or 3-ring aryl groups and substituted aryl groups:

$R^2$ and $R^4$; If $Q^2$ or $Q^3$ is O or S, none,
if $Q^2$ or $Q^3$ is either N or P, independently selected from H, $C_1$ to $C_{20}$ alkyl groups, 1-, 2- 3-ring aryl groups and substituted aryl groups;

$R^5$, $R^6$, and $R^7$; independently selected from H, $C_1$ to $C_{20}$ alkyl groups;

M: a first transition metal selected from the group consisting of Cr, Mn, V, Ni, Ti, Zr, Hf, Ta, and mixtures thereof;

L: each L independently selected from the group consisting of F, Cl, Br, I, $C_1$ to $C_{20}$ alkyl, $C_5$ to $C_{14}$ aryl, nitrate, $OR^{21}$, $OC(=O)R^{22}$; $R^{23}$; CN; SCN, CO, H, wherein $R^{21}$, $R^{22}$, and $R^{23}$ are independently selected from the group consisting of H, $C_1$ to $C_{20}$ alkyl groups, susbstituted alkyl groups, 1-, 2- or 3-ring aryl groups, substituted aryl groups, and silyl groups;

solvent: selected from the group consisting of ethers, polyethers, esters, alcohols halogenated hydrocarbons, and mixtures thereof;

q: 0–5 (integer) to balance overall electrical charge; and m: 0–10 (integer or fractional); and a co-catalyst consisting essentially of at least one organometallic compound.

11. The catalyst system of claim 10, wherein the olefin is selected from the group consisting of ethylene, propylene, 1-butene, cis-2-butene, trans-2-butene, 1-pentene, 1-hexene, 1-heptene, 1-octene, 1-nonene, 1-octadecene, 1,5-hexadiene, 1,4-hexadiene, 1,3-hexadiene, and mixtures thereof;

the organometallic compound is selected from the group consisting of organoaluminum compound, organoboron compound, organogallium compound, organotin compound, organozinc compound, organocadmium compound, organolithium compound, organosodium compound, organopotassium compound, organorubidium compound, organomagnesium compound, organocalcium compound and mixtures thereof;

the product comprises α-olefins, linear, branched or mixtures thereof;

M is selected from the group consisting of chromium, vanadium, manganese, and mixtures thereof;

$Q^1$ and $Q^2$ are nitrogen, $Q^3$ is oxygen, and $R^4$ does not exist;

$R^1$ and $R^3$ are independently selected from $C_1$ to $C_5$ alkyl groups or 1–3 ring aryl groups;

$R^2$ has a structure of FORMULA C;

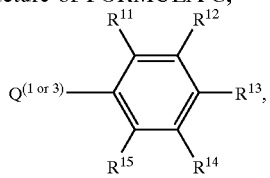

wherein $R^{11}$, $R^{12}$, $R^{13}$, $R^{14}$, and $R^{15}$ are individually selected from H, $C_1$ to $C_{20}$ alkyl groups, substituted $C_1$ to $C_{20}$ alkyl groups, 1–3 ring aryl groups, substituted 1–3 ring aryl groups, F, Cl, Br, I, amino groups, silyl groups such as $Si(CH_3)_3$, $Si(phenyl)_3$ and the like;

$R^5$ $R^6$, and $R^7$ are independently selected from H, and $C_1$ to $C_5$ alkyl groups; and each L is independently selected from F, Cl, Br, I, alkyl, aryl and mixtures thereof.

12. The catalyst system of claim 10, wherein the olefin is selected from the group consisting of ethylene, propylene, 1-butene, 1-hexene, 1-octadecene, and mixtures thereof;

the co-catalyst is selected from MAO, MMAO, and mixtures thereof;

the product comprises terminal olefin, which are linear, branched, or mixtures thereof;

the metal consists essentially of chromium;

$Q^1$ and $Q^2$ are nitrogen, $Q^3$ is oxygen, and $R^4$ does not exist;

$R^1$ and $R^3$ are independently selected from $C_1$ to $C_5$ alkyl groups or 1–3 ring aryl groups;

$R^2$ has a structure of FORMULA C;

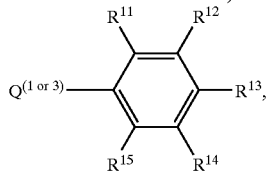

wherein $R^{12}$, $R^{13}$, and $R^{14}$ are H, and $R^{11}$ and $R^{15}$ are independently selected from the group consisting of methyl and iso-propyl groups;

$R^5$ $R^6$, and $R^7$ are H; and

L consists essentially of Cl.

13. A multi-component catalyst system comprising:

(a) at least one first component consisting essentially an ethylene or propylene dimerization or trimerization catalyst comprising a metal-tridentate ligand complex, wherein the complex comprises a first transition metal, a tridentate ligand having nitrogen for all three coordinating sites in the tridentate ligand, and wherein the metal-tridentate ligand complex has a formula as FORMULA B;

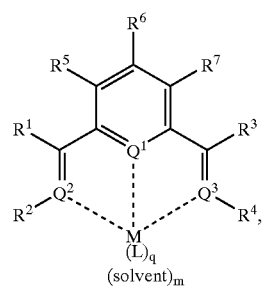

wherein $Q^1$, $Q^2$, and $Q^3$; independently selected from O, S, N, and P;

$R^1$ and $R^3$; independently selected from H, $C_1$ to $C_{20}$ alkyl groups, 1-, 2- or 3-ring aryl groups and substituted aryl groups;

$R^2$ and $R^4$; if $Q^2$ or $Q^3$ is O or S, none,
if or $Q^2$ or $Q^3$ is either N or P, independently selected from H, $C_1$ to $C_{20}$ alkyl groups, 1-, 2- or 3-ring aryl groups and substituted aryl groups;

$R^5$, $R^6$, and $R^7$; independently selected from H, $C_1$ to $C_{20}$ akyl groups;

M: a first transition metal selected from the group consisting of Cr, Mn, V, Ni, Ti, Zr, Hf, Ta, and mixture thereof;

L each L independently selected from the group consisting of F, Cl, Br, L $C_1$ to $C_{20}$ alkyl, $C_5$ to $C_{14}$ aryl, nitrate, $OR^{21}$, $OC(=O)R^{22}$; $R^{23}$; CN; SCN, CO, H, wherein $R^{21}$, $R^{22}$, and $R^{23}$ are independently selected from the group consisting of H, $C_1$ to $C_{20}$ alkyl groups, substituted alkyl group 1-, 2- or 3-ring aryl groups, substituted aryl groups, and silyl groups;

solvent; selected from the group consisting of ethers, polyethers, esters, alcohols, halogenated hydrocarbons, and mixtures thereof;

g: 0–5 (integer) to balance overall electrical charge;

m: 0–10 (integer or fractional); and (b) at least one second component having a second transition metal selected from the group consisting of a Ziegler-Natta catalyst, a precursor of the Ziegler-Natta catalyst, a metallocene, a precursor of the metallocene, a second metal-tridentate ligand complex wherein not all three coordinating sites are the same, and mixtures thereof.

14. The multi-component catalyst system of claim 13, wherein the first transition metal is selected from the group consisting of manganese, chromium, vanadium, nickel, and mixtures thereof; and the second transition metal is selected from the group consisting of titanium, zirconium, hafnium, vanadium, and mixtures thereof.

15. The multi-component catalyst of claim 14, wherein the multi-component catalyst system is used in the presence of a co-catalyst comprising at least one organometallic compound to polymerize ethylene or propylene into a product characterized by having branching along main polymer chains and being selected from the group consisting of polyethylene (PE), low density polyethylene (LDPE), linear low density polyethylene (LLDPE), polypropylene (PP), wax, and mixtures thereof.

* * * * *